US00PP24304P2

(12) United States Plant Patent
Beekenkamp

(10) Patent No.: US PP24,304 P2
(45) Date of Patent: Mar. 11, 2014

(54) ***BEGONIA* PLANT NAMED 'BKBEWFAFSP'**

(50) Latin Name: *Begonia pendula*
Varietal Denomination: BKBEWFAFSP

(75) Inventor: Annie Cornelia Beekenkamp, Maasdijk (NL)

(73) Assignee: Beekenkamp Plants B.V., Maasdijk (NL)

( * ) Notice: Subject to any disclaimer, the term of this patent is extended or adjusted under 35 U.S.C. 154(b) by 14 days.

(21) Appl. No.: 13/507,637

(22) Filed: Jul. 13, 2012

(51) Int. Cl.
*A01H 5/00* (2006.01)

(52) U.S. Cl.
USPC ..... Plt./343

(58) Field of Classification Search
USPC ..... Plt./343
See application file for complete search history.

*Primary Examiner* — Kent L Bell
(74) *Attorney, Agent, or Firm* — C. A. Whealy

(57) ABSTRACT

A new and distinct cultivar of *Begonia* plant named 'BKBEWFAFSP', characterized by its upright, outwardly spreading to pendulous plant habit; moderately freely basal branching habit; medium-size leaves; freely and continuously flowering habit; flowers that are light pink in color with darker pink-colored margins; long flowering period; and good garden performance.

2 Drawing Sheets

Botanical designation: *Begonia pendula.*
Cultivar denomination: 'BKBEWFAFSP'.

BACKGROUND OF THE INVENTION

The present invention relates to a new and distinct cultivar of *Begonia* plant, botanically known as *Begonia pendula* and hereinafter referred to by the name 'BKBEWFAFSP'.

The new *Begonia* plant is a product of a planned breeding program conducted by the Inventor in Amstelveen, The Netherlands. The objective of the breeding program was to develop new hanging basket *Begonia* plants with good summer performance and long flowering period.

The new *Begonia* plant originated from a cross-pollination made by the Inventor in March, 2007 of a proprietary selection of *Begonia pendula* identified as code number 07-002-04, not patented, as the female, or seed, parent with a proprietary selection of *Begonia pendula* identified as code number 06-276-08, not patented, as the male, or pollen, parent. The new *Begonia* plant was discovered and selected by the Inventor as a single flowering plant from within the progeny of the stated cross-pollination in a controlled greenhouse environment in Amstelveen, The Netherlands in April, 2008.

Asexual reproduction of the new *Begonia* plant by tip cuttings in a controlled greenhouse environment in Amstelveen, The Netherlands since May, 2009 has shown that the unique features of this new *Begonia* plant are stable and reproduced true to type in successive generations.

SUMMARY OF THE INVENTION

Plants of the new *Begonia* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'BKBEWFAFSP'. These characteristics in combination distinguish 'BKBEWFAFSP' as a new and distinct *Begonia* plant:

1. Upright, outwardly spreading to pendulous plant habit.
2. Moderately freely basal branching habit.
3. Medium-size leaves.
4. Freely and continuously flowering habit.
5. Flowers that are light pink in color with darker pink-colored margins.
6. Long flowering period; plants flower throughout the summer in The Netherlands.

Plants of the new *Begonia* can be compared to plants of the female parent selection. Plants of the new *Begonia* differ primarily from plants of the female parent selection in the following characteristics:

1. Plants of the new *Begonia* have darker green-colored leaves than plants of the female parent selection.
2. Leaves of plants of the new *Begonia* are slightly pubescent whereas leaves of plants of the female parent selection are glabrous.
3. Plants of the new *Begonia* and the female parent selection differ in flower color as plants of the female parent selection have pale orange-colored flowers.

Plants of the new *Begonia* can be compared to plants of the male parent selection. Plants of the new *Begonia* differ primarily from plants of the male parent selection in flower color as plants of the male parent selection have white-colored flowers.

Plants of the new *Begonia* can be compared to plants of the *Begonia* 'Rainbow Falls', not patented. In side-by-side comparisons conducted in Amstelveen, The Netherlands, plants of the new *Begonia* differed from plants of 'Rainbow Falls' in the following characteristics:

1. Plants of the new *Begonia* had semi-double type flowers whereas plants of 'Rainbow Falls' had double type flowers.
2. Plants of the new *Begonia* and 'Rainbow Falls' differed in flower color as plants of 'Rainbow Falls' had yellow and pink-colored flowers.

Plants of the new *Begonia* can be compared to plants of the *Begonia* 'BKBEWPF', disclosed in U.S. Plant Pat. No. 23,138. In side-by-side comparisons conducted in Amstelveen, The Netherlands, plants of the new *Begonia* differed from plants of 'BKBEWPF' in the following characteristics:

1. Plants of the new *Begonia* were more compact than plants of 'BKBEWPF'.
2. Flowers of plants of the new *Begonia* had fewer tepaloids than flowers of plants of 'BKBEWPF'.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet comprises a side perspective view of a typical flowering plant of 'BKBEWFAFSP' grown in a container.

The photograph on the second sheet is a close up view of the upper and lower surfaces of typical flower buds, flowers and leaves of 'BKBEWFAFSP'.

DETAILED BOTANICAL DESCRIPTION

Plants used for the aforementioned photographs and following observations and measurements were grown in 12-cm containers during the winter in a glass-covered greenhouse in Maasdijk, The Netherlands. During the production of the plants, day and night temperatures ranged from 18° C. to 19° C. Plants were eight weeks old when the photographs and the description were taken. In the following description, color references are made to The Royal Horticultural Society Colour Chart, 2007 Edition, except where general terms of ordinary dictionary significance are used.

Botanical classification: *Begonia pendula* 'BKBEWFAFSP'.

Parentage:

*Female, or seed, parent*.—Proprietary selection of *Begonia pendula* identified as code number 07-002-04, not patented.

*Male, or pollen, parent*.—Proprietary selection of *Begonia pendula* identified as code number 06-276-08, not patented.

Propagation:

*Type*.—By tip cuttings.

*Time to initiate roots, summer*.—About one week at temperatures of about 20° C. to 25° C.

*Time to initiate roots, winter*.—About one week at temperatures of about 18° C. to 20° C.

*Time to produce a rooted young plant, summer*.—About 32 days at temperatures of about 20° C. to 25° C.

*Time to produce a rooted young plant, winter*.—About 35 days at temperatures of about 18° C. to 20° C.

*Root description*.—Medium in thickness, fibrous; white in color; plants of the new *Begonia* have not been observed to form tubers.

*Rooting habit*.—Moderate branching; medium density.

Plant description:

*Plant form and growth habit*.—Upright, outwardly spreading to pendulous plant habit; plant shape roughly flattened globular; moderately freely basal branching with about seven basal branches per plant; moderately vigorous growth habit.

*Plant height*.—About 14.9 cm.

*Plant width*.—About 31.5 cm.

*Branch description*.—Length: About 10.1 cm. Diameter: About 7 mm. Internode length: About 1.5 cm. Texture: Smooth, glabrous. Aspect: Upright to about 30° from vertical. Color, developing: Between 152B and 197A to 197B. Color, fully developed: Between 152A to 197A.

*Leaf description*.—Arrangement: Alternate, simple. Length: About 12.7 cm. Width: About 6.2 cm. Shape: Ovate. Apex: Acuminate. Base: Oblique. Margin: Biserrate. Texture, upper surface: Smooth, glabrous; velvety. Texture, lower surface: Sparsely pubescent. Venation pattern: Palmate; reticulate. Color: Developing leaves, upper surface: Close to 147A. Developing leaves, lower surface: Close to 184B. Fully expanded leaves, upper surface: Darker than between 147A and N189A; venation, close to 147A. Fully expanded leaves, lower surface: Close to 183C to 183D; venation, close to 148A, veins surrounded by close to 147B. Petioles: Length: About 4.7 cm. Diameter: About 4 mm. Texture, upper and lower surfaces: Sparsely pubescent. Color, upper surface: Close to 199A slightly tinged with close to 152A. Color, lower surface: Close to 199A.

Flower description:

*Flowering habit*.—Female rotate and male cruciform flowers arranged in axillary compound cymes; freely flowering habit with about four flowers per cyme and about 120 flowers developing per plant; flowers face outwardly to drooping.

*Fragrance*.—None detected.

*Natural flowering season*.—Plants begin flowering about 45 days after planting; long flowering period, plants flower freely and continuously from spring until October in The Netherlands.

*Flower longevity*.—Individual flowers last about ten days on the plant; flowers not persistent.

*Inflorescence height*.—About 13.4 cm.

*Inflorescence diameter*.—About 13.4 cm.

*Female flowers*.—Diameter: About 7.3 cm. Height: About 2.1 cm. Flower buds: Length: About 2.5 cm. Diameter: About 1.2 cm. Shape: Ovate. Color: Close to 49B to 49C; towards the margins, tinged with close to 50C; towards the base, close to 149D. Tepals: Quantity per flower and arrangement: About five in a single whorl. Length: About 4.2 cm. Width: About 1.6 cm. Shape: Obovate to narrowly obovate. Apex: Obtuse to emarginate or praemorse. Margin: Entire. Texture, upper and lower surfaces: Smooth, glabrous; slightly velvety. Color: When opening, upper surface: Close to 55D; margins, close to 55B. When opening, lower surface: Close to 55C; margins, close to 55A to 55B. Fully opened, upper surface: Close to 56D; margins, close to 55A; color does not change with development. Fully opened, lower surface: Close to 54C; color does not change with development.

*Male flowers*.—Diameter: About 8.2 cm. Height: About 2.4 cm. Flower buds: Length: About 2 cm. Diameter, flattened: About 1.4 cm. Shape, flattened: Broadly obovate. Color: Close to 49B to 49C; towards the margins, tinged with close to 50C; towards the base, close to 149D. Tepals: Quantity per flower and arrangement: About four in a single whorl; two tepals, broadly obovate in shape and two tepals, obovate in shape. Broadly obovate tepals: Length: About 4.3 cm. Width: About 3.1 cm. Apex: Obtuse to emarginate or praemorse. Margin: Entire. Texture, upper and lower surfaces: Smooth, glabrous; slightly velvety. Color: When opening, upper surface: Close to N155B; margins, close to 55B. When opening, lower surface: Close to 56A; margins, close to 55A to 55B. Fully opened, upper surface: Close to 56B; margins, close to 54A to 54B; color does not change with development. Fully opened, lower surface: Close to 52C; margins, close to 52A to 52B; color does not change with development. Obovate tepals: Length: About 4.1 cm. Width: About 1.9 cm. Apex: Obtuse to emarginate or praemorse. Margin: Entire. Texture, upper and lower surfaces: Smooth, glabrous; slightly velvety. Color: When opening, upper surface: Close to N155B. When opening, lower surface: Close to 56A. Fully opened, upper surface: Close to 56D; color does not change with development. Fully opened, lower surface: Close to 55C; color does not change with development.

*Tepaloids*.—Tepaloid development has been observed only on male flowers of the new *Begonia* plant. Quantity per flower and arrangement: About six in a single whorl. Length: About 2 cm. Width: About 9 mm. Shape: Narrowly obovate. Apex: Obtuse to emarginate or praemorse. Margin: Entire. Texture, upper and lower surfaces: Smooth, glabrous; slightly velvety. Color: When opening, upper surface: Close to N155B. When opening, lower surface: Close to 56A. Fully opened, upper surface: Close to 56D; color does not change with development. Fully opened, lower surface: Close to 55C; color does not change with development.

*Peduncles*.—Length: About 7.2 cm. Diameter: About 4 mm. Angle: About 30° from branch axis. Texture: Smooth, glabrous. Color: Close to 152B.

*Pedicels*.—Length: About 4.2 cm. Diameter: About 1.75 mm. Angle: About 45° from the peduncle axis. Texture: Smooth, glabrous. Color: Close to 42B.

*Reproductive organs*.—Stamens: Present on male flowers only. Number of stamens: About 50 per flower. Filament length: About 5 mm. Filament color: Close to 13C. Anther length: About 1 mm. Anther shape: Club-shaped. Anther color: Close to 11B. Pollen amount: Scarce. Pollen color: Close to 11B. Pistils: Present on female flowers only. Quantity per flower: About six. Length: About 9 mm. Style length: About 5 mm. Style color: Close to 1B. Stigma color: Close to 12A. Ovary color: Close to 145A.

*Seeds and fruits*.—Seed and fruit development production has not been observed on plants of the new *Begonia*.

Disease & pest resistance: Resistance to pathogens and pests common to *Begonia* has not been observed on plants of the new *Begonia*.

Garden performance: Plants of the new *Begonia* have been observed to have good garden performance and to tolerate temperatures from about 14° C. to about 35° C.

It is claimed:

1. A new and distinct *Begonia* plant named 'BKBEW-FAFSP' as illustrated and described.

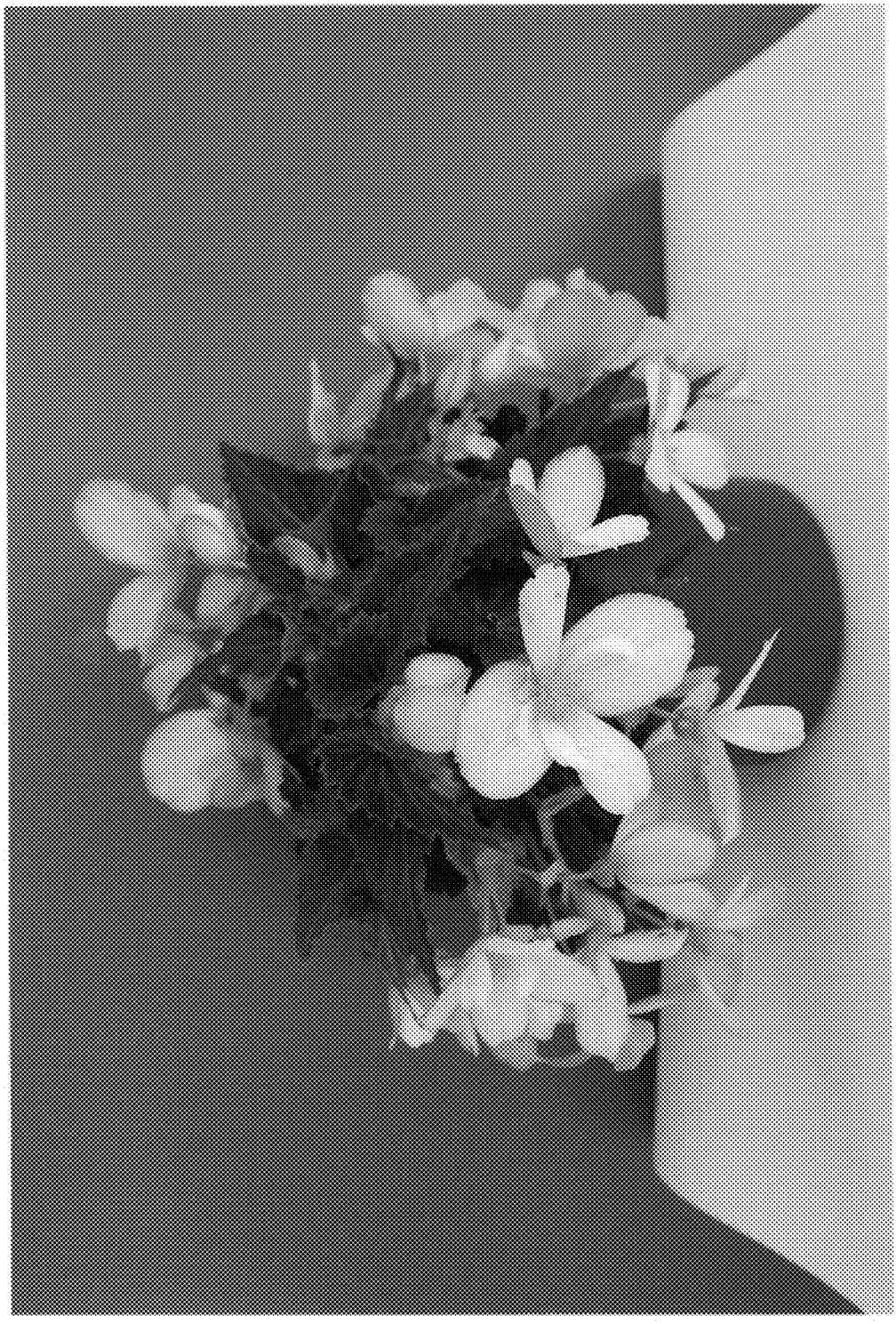

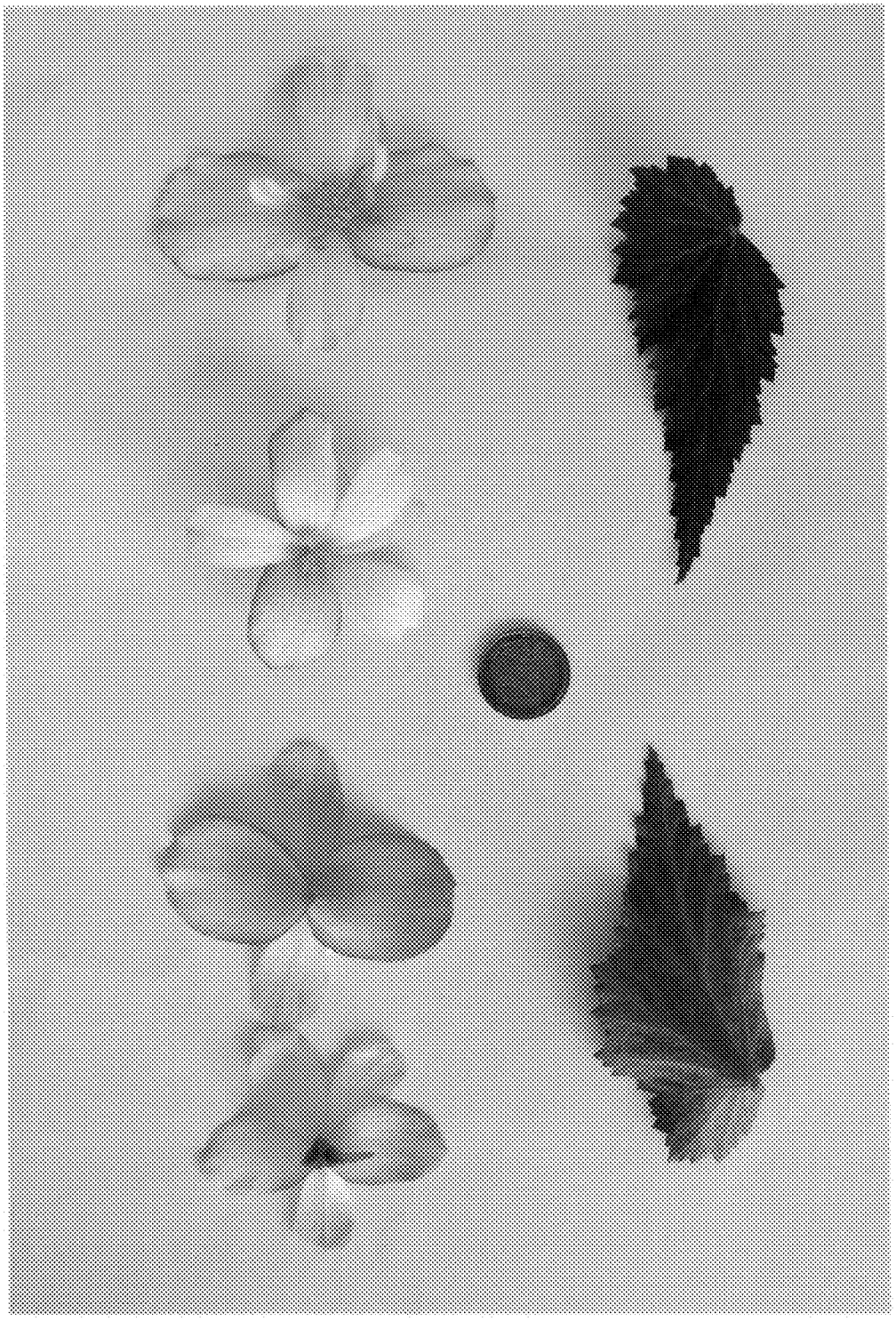

* * * * *